United States Patent [19]

Tsujimoto et al.

[11] Patent Number: 5,506,344

[45] Date of Patent: Apr. 9, 1996

[54] ANTIBODIES SPECIFIC FOR BCL-2 GENE PRODUCT

[75] Inventors: Yoshihide Tsujimoto, Landsdowne; Carlo A. Croce, Philadelphia, both of Pa.

[73] Assignee: The Wistar Institute, Philadelphia, Pa.

[21] Appl. No.: 435,193

[22] Filed: May 5, 1995

Related U.S. Application Data

[62] Division of Ser. No. 228,704, Apr. 18, 1994, which is a continuation of Ser. No. 994,941, Dec. 23, 1992, which is a continuation of Ser. No. 663,010, Mar. 19, 1991, Pat. No. 5,202,429, which is a continuation of Ser. No. 883,687, Jul. 9, 1986, Pat. No. 5,015,568.

[51] Int. Cl.$^6$ ..................... C07K 16/18; A61K 39/395; C12N 5/20

[52] U.S. Cl. .................. 530/388.85; 530/387.7; 530/387.9; 530/388.8; 530/389.7; 424/138.1; 424/155.1; 424/156.1; 435/70.21; 435/172.2; 435/240.27

[58] Field of Search ............... 424/138.1, 139.1, 424/152.1, 155.1, 174.1, 156.1; 435/70.21, 172.2, 240.27; 530/387.1, 388.8, 389.7, 350, 387.7, 388.1, 388.85, 387.9

[56] References Cited

PUBLICATIONS

Tsujimoto et al., "Analysis of the Structure, Transcripts, and Protein Products of bcl-2, the Gene Involved in Human Follicular Lymphoma", *Proc. Natl. Acad. Sci. USA* 83:5214–5218 (1986).
Tsujimoto et al., "The t(14;18) Chromosome Translocations Involved in B-Cell Neoplasms Result from Mistakes in VDJ Joining", *Science*, 229:1390–1393 (1985).
Tsujimoto et al., "DNA Rearrangements in Human Follicular Lymphoma can Involve the 5' or the 3' region of the bcl-2 Gene", *Proc. Natl. Acad. Sci. USA* 84:1329–1331 (1987).
Tsujimoto et al., "Clustering of Breakpoints on Chromosome II in Human B-Cell Noeplasms with the t(11;14) Chromosome Translocation", *Nature* 315:340–343 (1985).
Tsujimoto et al., "Involvement of the bcl-2 Gene in Human Follicular Lymphoma", *Science* 228:1440–1443 (1985).
Tsujimoto et al., "Cloning of the Chromosome Breakpoint of Neoplastic B Cells with the t(14;18) Chromosome Translocation", *Science* 226:1097–1099 (1984).
Pegoraro et al., "A 14;18 and an 8;14 Chromosome Translocation in a Cell Line Derived from an Acute B-Cell Leukemia", *Proc. Natl. Acad. Sci. USA* 81:7166–7170 (1984).
Cleary et al., "Nucleotide Sequence of a t(14;18) Chromosomal Breakpoint in Follicular Lymphoma and Demonstration of a Breakpoint-Cluster Region Near a Transcriptionally Active Locus on Chromosome 18", *Proc. Natl. Acad. Sci. USA* 82:7439–7443 (1985).
Ngan et al., *New England Journal of Medicine* 318:1638–1644 (1988).
Reed et al., *Nature* 336: 259–261 (1988).

*Primary Examiner*—Robert D. Budens
*Assistant Examiner*—Julie E. Reeves
*Attorney, Agent, or Firm*—Banner & Allegretti, Ltd.

[57] ABSTRACT

The sequence of the protein coding regions of the bcl-2 gene are provided as well as bacterial clones which produce the proteins. Assays are provided for detecting a class of B-cell neoplasms associated with a chromosome translocation between chromosomes 14 and 18. This translocation is involved in the majority of cases of human follicular lymphomas. One assay employs an antibody which is immunoreactive with a human protein which is over-expressed due to the chromosome translocation. Another assay involves measurement of the amount of mRNA which hybridizes to the gene proximal to the translocation breakpoint.

4 Claims, 6 Drawing Sheets

```
                                                  GCGCCCGC
CCCTCCGCGC  CGCCTGCCCG  CCCGCCCGCC  GCGCTCCCGC  CCGCCGCTCT    -1401
CCGTGGCCCC  GCCGCGCTGC  CGCCGCCGCC  GCTGCCAGCG  AAGGTGCCGG
GGCTCCGGGC  CCTCCCTGCC  GGCGGCCGTC  AGCGCTCGGA  GCCAACTGCG
CGACGGGAGG  TCCGGGAGGC  GACCGTAGTC  GCGCCGCCGC  GCAGGACCAG
GAGGAGGAGA  AAGGGTGCGC  AGCCCGGAGG  CCGGGTGCGC  CGGTGGGGTC
CAGCGGAAGA  GGGGGTCCAG  GGGGGAGAAC  TTCGTAGCAG  TCATCCTTTT
TAGGAAAAGA  GGGAAAAAAT  AAAACCCTCC  CCCACCACCT  CCTTCTCCCC
ACCCCTCGCC  GCACCACACA  CAGCGCGGGC  TTCTAGCGCT  CGGCACCGGC
GGGCCAGGCG  CGTCCTGCCT  TCATTTATCC  AGCAGCTTTT  CGGAAAATGC    -1001

ATTTGCTGTT  CGGAGTTTAA  TCAGAAGACG  ATTCCTGCCT  CCGTCCCCGG
CTCCTTCATC  GTCCCATCTC  CCCTGTCTCT  CTCCTGGGGA  GGCGTGAAGC
GGTCCCGTGG  ATAGAGATTC  ATGCCTGTGT  CCGCGCGTGT  GTGCGCGCGT
ATAAATTGCC  GAGAAGGGGA  AAACATCACA  GGACTTCTGC  GAATACCGGA
CTGAAAATTG  TAATTCATCT  GCCGCCGCCG  CTGCCAAAAA  AAAACTCGAG
CTCTTGAGAT  CTCCGGTTGG  GATTCCTGCG  GATTGACATT  TCTGTGAAGC
AGAAGTCTGG  GAATCGATCT  GGAAATCCTC  CTAATTTTTA  CTCCCTCTCC
CCCCGACTCC  TGATTCATTG  GGAAGTTTCA  AATCAGCTAT  AACTGGAGAG
TGCTGAAGAT  TGATGGGATC  GTTGCCTTAT  GCATTTGTTT  TGGTTTTACA
AAAAGGAAAC  TTGACAGAGG  ATCATGCTGT  ACTTAAAAAA  TACAAGTAAG     -501

TCTCGCACAG  GAAATTGGTT  TAATGTAACT  TTCAATGGAA  ACCTTTGAGA
TTTTTTACTT  AAAGTGCATT  CGAGTAAATT  TAATTTCCAG  GCAGCTTAAT
ACATTGTTTT  TAGCCGTGTT  ACTTGTAGTG  TGTATGCCCT  GCTTTCACTC
AGTGTGTACA  GGGAAACGCA  CCTGATTTTT  TACTTATTAG  TTTGTTTTTT
CTTTAACCTT  TCAGCATCAC  AGAGGAAGTA  GACTGATATT  AACAATACTT
ACTAATAATA  ACGTGCCTCA  TGAAATAAAG  ATCCGAAAGG  AATTGGAATA
AAAATTTCCT  GCGTCTCATG  CCAAGAGGGA  AACACCAGAA  TCAAGTGTTC
CGCGTGATTG  AAGACACCCC  CTCGTCCAAG  AATGCAAAGC  ACATCCAATA
AAATAGCTGG  ATTATAACTC  CTCTTCTTTC  TCTGGGGCC   GTGGGGTGGG
AGCTGGGGCG  AGAGGTGCCG  TTGGCCCCCG  TTGCTTTTCC  TCTGGGAAGG      -1
```

FIG. 2A

```
  1 MET ALA HIS ALA GLY ARG THR GLY TYR ASP ASN ARG GLU ILE VAL
    ATG GCG CAC GCT GGG AGA ACG GGG TAC GAC AAC CGG GAG ATA GTC

MET LYS TYR ILE HIS TYR LYS LEU SER GLN ARG GLY TYR GLU TRP
 46 ATG AAG TAC ATC CAT TAT AAG CTG TCG CAG AGG GGC TAC GAG TGG

ASP ALA GLY ASP VAL GLY ALA ALA PRO PRO GLY ALA ALA PRO ALA
 91 GAT GCG GGA GAT GTG GGC GCC GCG CCC CCG GGG GCC GCC CCC GCA

PRO GLY ILE PHE SER SER GLN PRO GLY HIS THR PRO HIS PRO ALA
136 CCG GGC ATC TTC TCC TCC CAG CCC GGG CAC ACG CCC CAT CCA GCC

ALA SER ARG ASP PRO VAL ALA ARG THR SER PRO LEU GLN THR PRO
181 GCA TCC CGC GAC CCG GTC GCC AGG ACC TCG CCG CTG CAG ACC CCG

ALA ALA PRO GLY ALA ALA ALA GLY PRO ALA LEU SER PRO VAL PRO
226 GCT GCC CCC GGC GCC GCC GCG GGG CCT GCC CTC AGC CCG GTG CCA

PRO VAL VAL HIS LEU ALA LEU ARG GLN ALA GLY ASP ASP PHE SER
271 CCT GTG GTC CAC CTG GCC CTC CGC CAA GCC GGC GAC GAC TTC TCC

ARG ARG TYR ARG GLY ASP PHE ALA GLU MET SER SER GLN LEU HIS
316 CGC CGC TAC CGC GGC GAC TTC GCC GAG ATG TCC AGC CAC CTG CAC

LEU THR PRO PHE THR ALA ARG GLY ARG PHE ALA THR VAL VAL GLU
361 CTG ACG CCC TTC ACC GCG CGG GGA CGC TTT GCC ACG GTC GTG GAG

GLU LEU PHE ARG ASP GLY VAL ASN TRP GLY ARG ILE VAL ALA PHE
406 GAG CTC TTC AGG GAC GGG GTG AAC TGG GGG AGG ATT GTG GCC TTC

PHE GLU PHE GLY GLY VAL MET CYS VAL GLU SER VAL ASN ARG GLU
451 TTT GAG TTC GGT GGG GTC ATG TGT GTG GAG AGC GTC AAC CGG GAG

MET SER PRO LEU VAL ASP ASN ILE ALA LEU TRP MET THR GLU TYR
496 ATG TCG CCC CTG GTG GAC AAC ATC GCC CTG TGG ATG ACT GAG TAC

LEU ASN ARG HIS LEU HIS THR TRP ILE GLN ASP ASN GLY GLY TRP
541 CTG AAC CGG CAC CTG CAC ACC TGG ATC CAG GAT AAC GGA GGC TGG

ASP ALA PHE VAL GLU LEU TYR GLY PRO SER MET ARG PRO LEU PHE
586 GAT GCC TTT GTG GAA CTG TAC GGC CCC AGC ATG CGG CCT CTG TTT

ASP PHE SER TRP LEU SER LEU LYS THR LEU LEU SER LEU ALA LEU
631 GAT TTC TCC TGG CTG TCT CTG AAG ACT CTG CTC AGT TTG GCC CTG

VAL GLY ALA CYS ILE THR LEU GLY ALA TYR LEU SER HIS LYS
676 GTC GGA GCT TGC ATC ACC CTG GGT GCC TAT CTG AGC CAC AAG TGA
```

FIG. 2B

```
       AGTCAACATC CCTGCCCCAA ACAAATATGC
       AAAAGCTTCA CTAAAGCAGT AGAAATAATA TGCATTGTCA GTGATGTACC
       ATGAAACAAA GCTGCAGGCT GTTTAAGAAA AAATAACACA CATATAAACA
       TCACACACAC AGACAGACAC ACACACACAC AACAATTAAC AGTCTTCAGG
       CAAAACGTCG AATCAGCTAT TTACTGCCAA AGGGAAATAT CATTTATTTT
       TTACATTATT AAGAAAAAAG ATTTATTTAT TTAAGACAGT CCCATCAAAA

1001   CTCCGTCTTT GGAAATCCGA CCACTAATTG CCAAACACCG CTTCGTGTGG
       CTCCACCTGG ATGTTCTGTC CCTGTAAACA TAGATTCGCT TTCCATGTTG
       TTGCCGGAT CACCATCTGA AGAGCAGACG GATCGAAAAA GGACCTGATC
       ATTGCGGAAG CTGGCTTTCT GGCTGCTGGA GGCTGGGGAG AAGGTGTTCA
       TTCACTTGCA TTTCTTTGCC CTGGGGGCGT GATATTAACA GAGGGAGGGT
       TCCCGTGGGG GGAAGTCCAT GCCTCCCTGG CCTGAAGAAG AGACTCTTTG
       CATATGACTC ACATGATGCA TACCTGGTGG GAGGAAAAGA GTTGGGAACT
       TCAGATGGAC CTAGTACCCA CTGAGATTTC CACGCCGAAG GACAGCGATG
       GGAAAAATGC CCTTAAATCA TAGGAAAGTA TTTTTTTAAG CTACCAATTG
       TGCCGAGAAA AGCATTTTAG CAATTTATAC AATATCATCC AGTACCTTAA

1501   ACCCTGATTG TGTATATTCA TATATTTTGG ATACGCACCC CCCAACTCCC
       AATACTGGCT CTGTCTGAGT AAGAAACAGA ATCCTCTGGA ACTTGAGGAA
       GTGAACATTT CGGTGACTTC CGATCAGGAA GGCTAGAGTT ACCCAGAGCA
       TCAGGCCGCC ACAAGTGCCT GCTTTTAGGA GACCGAAGTC CGCAGAACCT
       ACCTGTGTCC CAGCTTGGAG GCCTGGTCCT GGAACTGAGC CGGGCCCTCA
       CTGGCCTCCT CCAGGGATGA TCAACAGGGT AGTGTGGTCT CCGAATGTCT
       GGAAGCTGAT GGATGGAGCT CAGAATTCCA CTGTCAAGAA AGAGCAGTAG
       AGGGGTGTGG CTGGCCTGT CACCCTGGGG CCCTCCAGGT AGGCCCGTTT
       TCACGTGGAG CATAGGAGCC ACGACCCTTC TTAAGACATG TATCACTGTA
       GAGGGAAGGA ACAGAGGCCC TGGGCCTTCC TATCAGAAGG ACATGGTGAA

2001   GGCTGGGAAC GTGAGGAGAG GCAATGGCCA CGGCCCATTT TGGCTGTAGC
       ACATGGCACG TTGGCTGTGT GGCCTTGGCC ACCTGTGAGT TTAAAGCAAG
       GCTTTAAATG ACTTTGGAGA GGGTCACAAA TCCTAAAAGA AGCATTGAAG
       TGAGGTGTCA TGGATTAATT GACCCCTGTC TATGGAATTA CATGTAAAAC
       ATTATCTTGT CACTGTAGTT TGGTTTTATT TGAAAACCTG ACAAAAAAAA
       AGTTCCAGGT GTGGAATATG GGGGTTATCT GTACATCCTG GGCATTAAA
       AAAAAATCAA TGGTGGGGAA CTATAAAGAA GTAACAAAAG AAGTGACATC
       TTCAGCAAAT AAACTAGGAA ATTTTTTTTT CTTCCAGTTT AGAATCAGCC
       TTGAAACATT GATGGAATAA CTCTGTGGCA TTATTGCATT ATATACCATT
       TATCTGTATT AACTTTGGAA TGTACTCTGT TCAATGTTTA ATGCTGTGGT
```

FIG. 2C

2501 TGATATTTCG AAAGCTGCTT TAAAAAAATA CATGCATCTC AGCGTTTTTT
TGTTTTTAAT TGTATTTAGT TATGGCCTAT ACACTATTTG TGAGCAAAGG
TGATCGTTTT CTGTTTGAGA TTTTTATCTC TTGATTCTTC AAAAGCATTC
TGAGAAGGTG AGATAAGCCC TGAGTCTCAG CTACCTAAGA AAAACCTGGA
TGTCACTGGC CACTGAGGAG CTTTGTTTCA ACCAAGTCAT GTGCATTTCC
ACGTCAACAG AATTGTTTAT TGTGACAGTT ATATCTGTTG TCCCTTTGAC
CTTGTTTCTT GAAGGTTTCC TCGTCCCTGG GCAATTCCGC ATTTAATTCA
TGGTATTCAG GATTACATGC ATGTTTGGTT AAACCCATGA GATTCATTCA
GTTAAAAATC CAGATGGCGA ATGACCAGCA GATTCAAATC TATGGTGGTT
TGACCTTTAG AGAGTTGCTT TACGTGGCCT GTTTCAACAC AGACCCACCC

3001 AGAGCCCTCC TGCCCTCCTT CGGCGGGGC TTTCTCATGG CTGTCCTTCA
GGGTCTTCCT GAAATGCAGT GGTCGTTACG CTCCACCAAG AAAGCAGGAA
ACCTGTGGTA TGAAGCCAGA CCTCCCCGGC GGGCCTCAGG GAACAGAATG
ATCAGACCTT TGAATGATTC TAATTTTTAA GCAAAATATT ATTTTATGAA
AGGTTTACAT TGTCAAAGTG ATGAATATGG AATATCCAAT CCTGTGCTGC
TATCCTGCCA AAATCATTTT AATGGAGTCA GTTTGCAGTA TGCTCCACGT
GGTAAGATCC TCCAAGCTGC TTTAGAAGTA ACAATGAAGA ACGTGGACGT
TTTTAATATA AAGCCTGTTT TGTCTTTTGT TGTTGTTCAA ACGGGATTCA
CAGAGTATTT GAAAAATGTA TATATATTAA GAGGTCACGG GGGCTAATTG
CTAGCTGGCT GCCTTTTGCT GTGGGTTTT GTTACCTGGT TTTAATAACA

3501 GTAAATGTGC CCAGCCTCTT GGCCCCAGAA CTGTACAGTA TTGTGGCTGC
ACTTGCTCTA AGAGTAGTTG ATGTTGCATT TTCCTTATTG TTAAAAACAT
GTTAGAAGCA ATGAATGTAT ATAAAAGCAA AAAAAAAAAA AAAAAA

FIG. 2D

```
TGATTGAAGACACCCCCTGGTCCAAGAATGCAAAGCCACATCCAATAAAATAGCTGGATTATAACTCTCTCTTCTTTCTCTG
                                                                              +1
CCCGCCGGTCGGGTGGGACCTCGGGCCGAGACGTGCGGGTTGGCCCCCGTTCCTTTTCCTCTCGGAACG MET ALA HIS
                                                                      ATG GCG CAC

ALA GLY ARG THR GLY TYR ASP ASN ARG GLU ILE VAL MET LYS TYR ILE HIS TYR LYS LEU
GCT GGC AGA ACG GGG TAC GAC AAC CGG GAG ATA GTG ATG AAG TAC ATC CAT TAT AAG CTG
                                    100
SER GLN ARG GLY TYR GLU TRP ASP ALA GLY ASP VAL GLY ALA ALA PRO PRO GLY ALA ALA
TCG CAG AGG GGC TAC GAG TGG GAT GCG GGA GAT GTG GGC GCC GCG CCC CCG GGG GCC GCC

PRO ALA PRO GLY ILE PHE SER SER GLN PRO GLY HIS THR PRO HIS PRO ALA ALA SER ARG
CCC GCA CCG GGC ATC TTC TCC TCC CAG CCC GGG CAC ACG CCC CAT CCA GCC GCA TCC CGC
              200
ASP PRO VAL ALA ARG THR SER PRO LEU GLN THR PRO ALA ALA PRO GLY ALA ALA ALA GLY
GAC CCG GTC GCC AGG ACC TCG CCG CTG CAG ACC CCG GCT GCC CCC GCC GCC GCC GCG GGG
                                                                          300
PRO ALA LEU SER PRO VAL PRO PRO VAL VAL HIS LEU ALA LEU ARG GLN ALA GLY ASP ASP
CCT GCG CTC AGC CCG GTG CCA CCT GTG GTC CAC CTG GCC CTC CGC CAA GCC GGC GAC GAC

PHE SER ARG ARG TYR ARG GLY ASP PHE ALA GLU MET SER SER GLN LEU HIS LEU THR PRO
TTC TCC CGC CGC TAC CGC GGC GAC TTC GCC GAG ATG TCC AGC CAG CTG CAC CTG ACG CCC
                                        400
PHE THR ALA ARG GLY ARG PHE ALA THR VAL VAL GLU GLU LEU PHE ARG ASP GLY VAL ASN
TTC ACC GCG CGG GGA CGC TTT GCC ACG GTG GTG GAG GAG CTC TTC ACG GAC GGG GTC AAC

TRP GLY ARG ILE VAL ALA PHE PHE GLU PHE GLY GLY VAL MET CYS VAL GLU SER VAL ASN
TGG GGC AGG ATT GTG GCC TTC TTT GAG TTC GGT GGG GTC ATG TGT GTG GAG AGC GTC AAC
              500
ARG GLU MET SER PRO LEU VAL ASP ASN ILE ALA LEU TRP MET THR GLU TYR LEU ASN ARG
CGG GAG ATG TCG CCC CTG GTG GAC AAC ATC GCC CTG TGG ATG ACT GAG TAC CTG AAC CGG
                                                                          600
HIS LEU HIS THR TRP ILE GLN ASP ASN GLY GLY TRP VAL GLY ALA SER GLY ASP VAL SER
CAC CTG CAC ACC TGC ATC CAG GAT AAC GGA GGC TGG GTA GGT GCA TCT GGT GAT GTG AGT
                                              ▲
LEU GLY GCG GGGCACAGGTCCGAGATCGGGGGTTGGAGTGCGGGTGGGCCTCCTCGGCAATGGGAGGCTGTGGAGCC
CTG GGC TGA
```

FIG. 3

ANTIBODIES SPECIFIC FOR BCL-2 GENE PRODUCT

This invention was made with government support under Grant CA 39860 from the National Cancer Institute. The United States Government has certain rights in this invention.

The application is a division of U.S. Ser. No. 08/228,704 filed Apr. 18, 1994, which is a continuation of Ser. No. 07/994,941 filed Dec. 23, 1992, which is a continuation of Ser. No. 07/663,010 filed Mar. 19, 1991, now U.S. Pat. No. 5,202,429 which is a continuation of Ser. No. 06/883,687 filed Jul. 9, 1986, now U.S. Pat. No. 5,015,568.

BACKGROUND OF THE INVENTION

Specific chromosomal rearrangements, predominantly translocations and inversions, are observed in the great majority of human hematopoietic malignancies. In Burkitt lymphoma the specific chromosomal translocations result in the juxtaposition of one of the three human immunoglobulin loci and the c-myc oncogene. In diffuse B-cell lymphomas, multiple myelomas and chronic lymphocytic leukemias of the B-cell type carrying the t(11;14) (q13;q32) chromosome translocation, the bcl-1 locus is translocated to the heavy-chain locus on chromosome 14. In most cases of follicular lymphoma, one of the most common human hematopoietic malignancies, a (t14;18) (q32;q21) chromosome translocation has been observed. This translocation moves the bcl-2 gene to a position adjacent to the heavy-chain locus. In one cell line derived from a leukemic patient having both a t(14;8) and a t(14;18) translocation enhanced mRNA production from the bcl-2 gene was observed. (Tsujimoto et al, Science, Vol. 228, pages 1440–1443 (1985).) It was concluded there that the transcription unit of the bcl-2 gene spans the chromosome break-point, and thus the oncogene protein is likely to be structurally altered in the B-cell neoplasms. Surprisingly, it has now been found that the translocation does not alter the oncogene protein itself, as the translocation break-points occur downstream from the actual protein coding sequences. Thus oncogenesis may be solely due to the overproduction of the normal human gene products of the bcl-2 gene.

Effective treatment for caner is often dependent upon an early and proper diagnosis of the malignancy. There is thus a need for simple and accurate diagnostic methods for detecting and identifying human malignancies, such as follicular lymphomas, in general, and follicular lymphomas in particular.

SUMMARY OF THE INVENTION

It is an object of the present invention to provide a diagnostic method for detecting B-cell neoplasms having t(14;18) translocations in a human.

It is another object of the present invention to provide a human bcl-2 gene which can be expressed in bacteria.

It is yet another object of the present invention to provide a substantially pure protein preparation of a bcl-2 gene product.

It is still another object of the present invention to provide a diagnostic method of detecting B-cell neoplasms employing an antibody which is immunoreactive with a bcl-2 gene product.

These and other objects of the invention are achieved by one or more of the following embodiments.

In one embodiment a diagnostic method for detecting B-cell neoplasms in a human is provided, comprising the steps of:

isolating B-cells from the human;

extracting proteins from said B-cells to form a test sample;

contacting said test sample with an antibody which is immunoreactive with a gene product of the bcl-2 gene, under conditions where antibody-antigen complexes are formed and are stable;

quantitating the amount of antibody-antigen complexes formed with said test sample; and comparing the amount of antibody-antigen complexes formed with said test sample to the amount formed with a control sample of proteins, a ratio of test sample complexes to control sample complexes of greater than about ten indicating B-cell neoplasm, said control sample of proteins extracted from cells selected from the group consisting of: B-cells from a normal human, cells from an established normal B-cell or pre- B-cell line, and non-B-cells from said human.

Also provided are forms of the human bcl-2 gene which are substantially free of introns. Such genes can be replicated and expressed in bacteria to form proteins having the same primary structure as the bcl-2 proteins produced in humans.

Also provided by the present invention are substantially pure preparations of proteins having an N-terminal end encoded by the first exon of the human bcl-2 gene.

In yet another embodiment of the present invention a diagnostic method for detecting B-cell neoplasms in a human is provided comprising the steps of:

isolating B-cells from the human, extracting-RNA from said B-cells to form a test sample;

contacting said test sample with a DNA probe containing a sequence of at least 15 neucleotides in length derived from the human bcl-2 gene, under conditions where homologous RNA-DNA hybrids form and are stable;

quantitating the amount of RNA-DNA hybrids formed with the test sample; and comparing the amount of RNA-DNA hybrids formed with said test sample to the amount formed with a control sample of RNA, a ratio of test sample hybrids to control sample hybrids of greater than about ten indicating B-cell neoplasm, said control sample of RNA extracted from cells selected from the group consisting of: B-cells from a normal human, cells from a normal B-cell or pre-B-cell line, and non-B-cells from said human.

BRIEF DESCRIPTION OF THE FIGURES

FIGS. 2A–2D show the nucleotide sequence of bcl-2 cDNA corresponding to the 5.5 kb transcript. Only the sequences surrounding the open reading frame are shown.

DETAILED DESCRIPTION OF THE INVENTION

According to one aspect of the present invention it has been discovered that B-cell neoplasms which are associated with t(14;18) chromosome translocations cause an increase in the expression of both the mRNA and the protein products of the bcl-2 gene. The expression in the neoplastic B-cells is generally about ten-fold higher than the amount expressed by normal cells. This elevated expression can be used as a diagnostic tool to detect the B-cell neoplasms in humans. Such neoplasms include follicular lymphomas as well as other lymphomas.

It has been found that three species of mRNA are transcribed from the bcl-2 gene. At least two different protein products have been identified. A 239 amino acid protein, designated bcl-2-alpha is translated from a 5.5 kb mRNA. A protein of 205 amino acids, bcl-2-beta is translated from a 3.5 kb mRNA. It is thought that bcl-2-alpha is also translated from the 8.5 kb mRNA species. All three size species of transcript share substantial sequence homology in the 5' portion of the gene, termed the first exon or 5' exon. The larger two transcripts appear to be spliced to a second exon which is at least 50 kb distal to the first. The splice site is in the midst of the protein coding sequence. Thus, the 3.5 kb transcript codes for a protein having a different carboxyl terminmus than the proteins coded by the two larger sized transcripts.

The hotspot for chomosome break-points among the t(14;18) translocations of follicular lymphomas map 3' to the protein coding region. Therefore it has now been found that the translocations do not alter the primary structure of the protein products.

Bacterial isolates available from the ATCC, under Accession Numbers 67147 and 67148, can be used to express bcl-2 gene products alpha and beta, respectively, in bacteria. The clones of the bcl-2 gene were obtained via cDNA cloning and so do not contain introns. Thus these clones can be expressed in bacteria to make products having the same primary sequence as those made in the human body. After growing the bacteria under suitable conditions which are well known in the art, the cells can be harvested and disrupted to extract total cellular protein. The protein can then, for example, be placed on a sizing column such as Sepharose™ or agarose beads, and proteins of the correct molecular weight, i.e., between abut 20 and 30 kD can be collected.

Further purification can be effected by use of an anti-bcl-2 antibody. Such an antibody can be used to immunoprecipitate bcl-2 proteins from the set of cellular proteins of the correct approximate molecular weight. Such antibodies can, for example, be raised against polypeptides synthesized according to the sequence shown in FIGS. 2A–2D. Alternatively, the antibodies can be raised against fusion proteins, which contain bcl-2 sequences as well as those of another protein. An example of an antibody raised to a fusion protein is discussed, infra. After immunoprecipitation, the bcl-2 proteins can be released from the antibodies to provide a substantially pure preparation of bcl-2 proteins.

If it is desired that bcl-2-alpha (approximately 26 kD) be separated from bcl-2-beta (approximately 22 kD) this separation can be achieved using either polyacrylamide gels or additional sizing or gel filtration columns. Of course, other separations are possible based on the inherent differences between the two proteins at their carboxyl termini. Techniques for using gel filtration columns and immunoprecipitation and antibody releasing are all well known in the art.

Any source of B-cells is suitable for use in the diagnostic test of this invention. B-cells can be isolated from the lymph nodes. Alternatively, the diagnostic test may employ a sample of peripheral blood obtained from an individual who is being screened for the presence of a B-cell neoplasm. Means for separating B-cells from the peripheral blood are well known in the art. For example, erythrocytes and granulocytes may be separated from the B-cells by centrifugation in a liquid having a density intermediate between the groups of cells to be separated.

Extraction of proteins from B-cells may be performed by any of the many means known in the art. For example, cells may be lysed by a detergent or by mechanical means. If desired, nucleic acids can be removed from the cell preparation by enzymatic digestion or by precipitation with agents such as streptomycin. Once again, such means are well known in the art.

Antibodies can be generated which are immunoreactive with the bcl-2 proteins by immunization of animals with a fusion protein consisting of a portion of the beta-galactosidase protein of E. coli and a portion of the human bcl-2 proteins. Preferably, the bcl-2 portion will contain sequences which are common to both bcl-2-alpha and bcl-2-beta. If desired, such a fusion protein can be purified using the properties which it shares with beta-galactosidase. Anti-sera raised against such a fusion protein in rabbits have been found to be immunoreactive with both bcl-2-alpha and bcl-2-beta in vitro. Furthermore, using this anti-sera in immunofluorescent techniques it is possible to determine cellular location of bcl-2 proteins in cells which have been fixed.

Antibodies can also be produced by immunization of animals, such as mice, rabbits and the like, with bcl-2-alpha, bcl-2-beta, fragments of them, or both. Alternatively, monoclonal antibodies can be generated using immortalized cell lines to provide uniform and continual antibody sources. Techniques for generating such antibodies are well known in the art. Appropriate antibodies can be screened using the natural gene products of bcl-2 or the fusion protein discussed above. While it is preferred that the antibody used in the diagnostic method immunoreact with both bcl-2-alpha and beta, an antibody may successfully be used which immunoreacts with only one of them.

The extracted proteins from the B-cells may be contacted with the antibody under suitable conditions for antibody-antigen complex formation. Generally, such conditions are physiological conditions. The protein extract may be bound to a solid support such as a nitrocellulose filter or a microtiter plate.

The antibody will generally bear a "tag" such as a radiolabel, a fluorescent label or an enzyme conjugate which under appropriate conditions produces a colored reaction product. Once again, such "tags" are quite well known in the art. Alternatively, if the antibody is not tagged, it can be detected by means of a second antibody from another species which is reacted with the first antibody. Of course, it is preferred for means of this diagnostic method that the immunological technique be as quantitatively sensitive as possible.

Means of detection of the antibody-antigen complexes will depend upon the method of tagging used for the antibody. For example, radiolabel tags can be detected by autoradiography or scintillation counting, while the products of enzyme-linked antibodies can be detected spectrophotometrically.

A parallel sample to the test sample is employed to provide the control. The control sample consists of an equivalent amount of proteins extracted from cells, preferably in the same manner as those of the test sample. The amount of protein can readily be determined employing techniques well known in the art, such as the Lowry or Bradford techniques. The cells used for preparing the control sample may be selected from the group consisting of B-cells from a normal human, cells from an established normal B-cell or pre-B-cell line, and non-B-cells from the human who is being screened for the neoplasm.

It is a finding of the present invention that in cases where a translocation has occurred between chromosomes 14 and 18, the level of bcl-2 protein detected immunologically in the B-cells is at least 10-fold higher than the amount of bcl-2 protein found in normal B-cells, in pre-B-cells, or in other non-B-cells from the same human.

To screen for elevated levels of mRNA transcribed from the bcl-2 gene, again one must isolate B-cells from the human who is to be screened. Any of the many methods known in the art are suitable. Total RNA extracted from the B-cells may be used, or alternatively mRNA may be isolated from the total cellular RNA. The mRNA may be purified, for example, by affinity chromatography on oligo(dT) cellulose which binds to the poly(A) tract at the 3' end of most mRNA. As is well known to those of skill in the art, it is essential that ribonuclease activity be minimized during preparation and assaying.

A DNA probe may be selected from any of the protein coding sequences of the bcl-2 gene. Preferably, the probe will be selected from sequences of the 5' or first exon of the gene, so that all three species of RNA can be detected. Alternatively the probe can be selected from sequences which hybridize exclusively with the 3.5 kb transcript or only with the 5.5 kb and the 8.5 kb transcript. Preferably the probe contains at least 15 nucleotides of the bcl-2 sequence. Suitable plasmid molecules which may be used as probes have been deposited at the ATCC under Deposit Numbers 67147 and 67148. Of course, other suitable probes may be synthesized or derived from these or other bcl-2 sequences. In order to perform the hybridization it is desirable that the probe be single stranded. Thus if the probe is double stranded, it should be denatured to single stranded form. Means for denaturing are well known in the art, including alkali or heat treatment. The probe can then be contacted with the RNA derived from the B-cells under conditions where homologous RNA-DNA hybrids form and are stable. Such conditions are well known in the art. Means for detecting hybrids are many and well known, but often involve use of radiolabeled probes and nucleases which degrade single stranded DNA. Other methods may be used.

Control samples can be derived from any of the cell sources described above for use in the antibody diagnostic test. Samples and control should be prepared in parallel under similar conditions. If comparison of the test and control sample hybridization shows a greater than about a ten-fold excess in the test sample, a B-cell neoplasm is indicated.

The following examples do not limit the scope of the invention but are merely illustrative.

EXAMPLE 1

Figure 1:
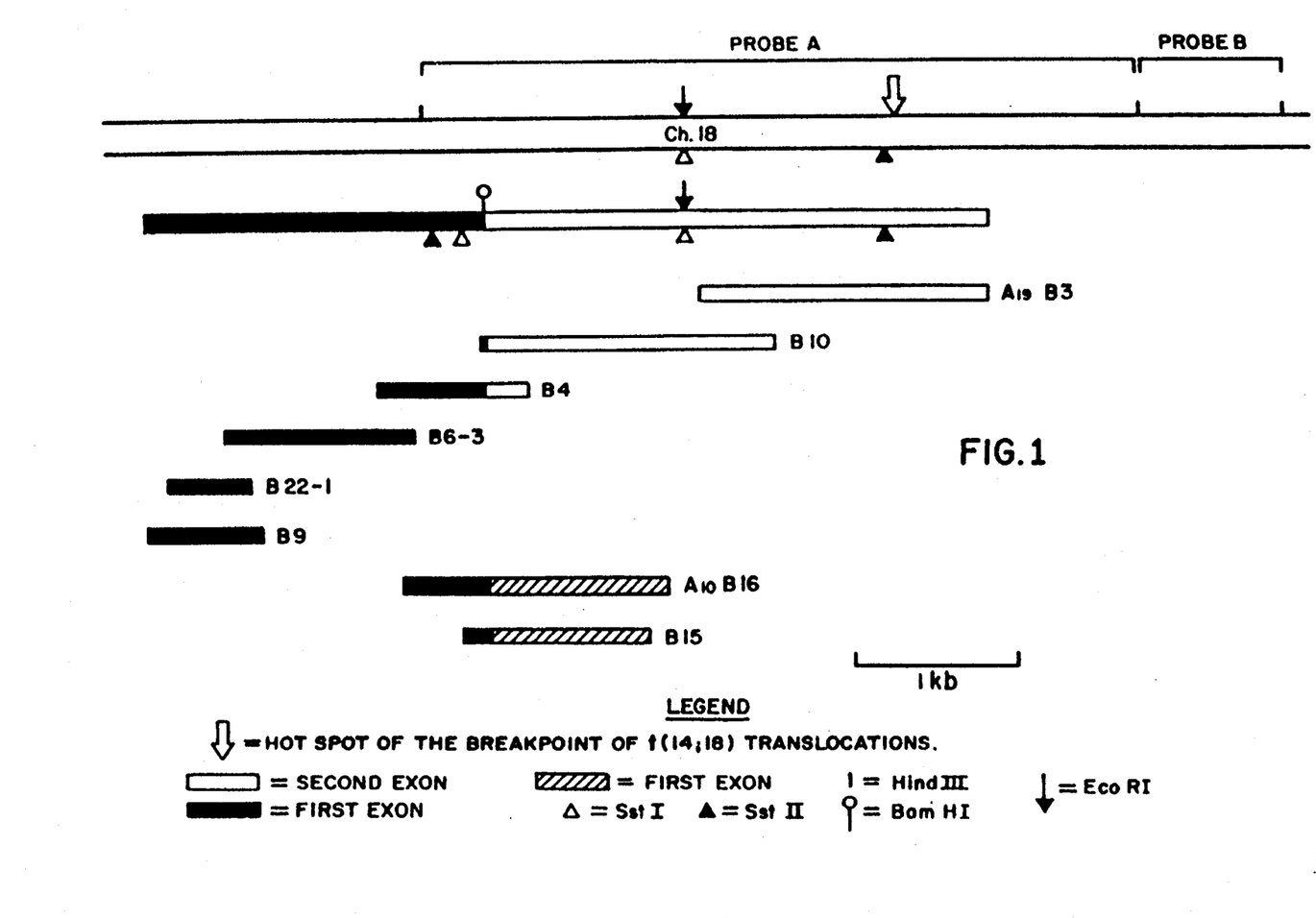
FIG. 1 shows a genomic restriction map of chromosome 18, and the structure of cDNA clones.
Figure 2D:
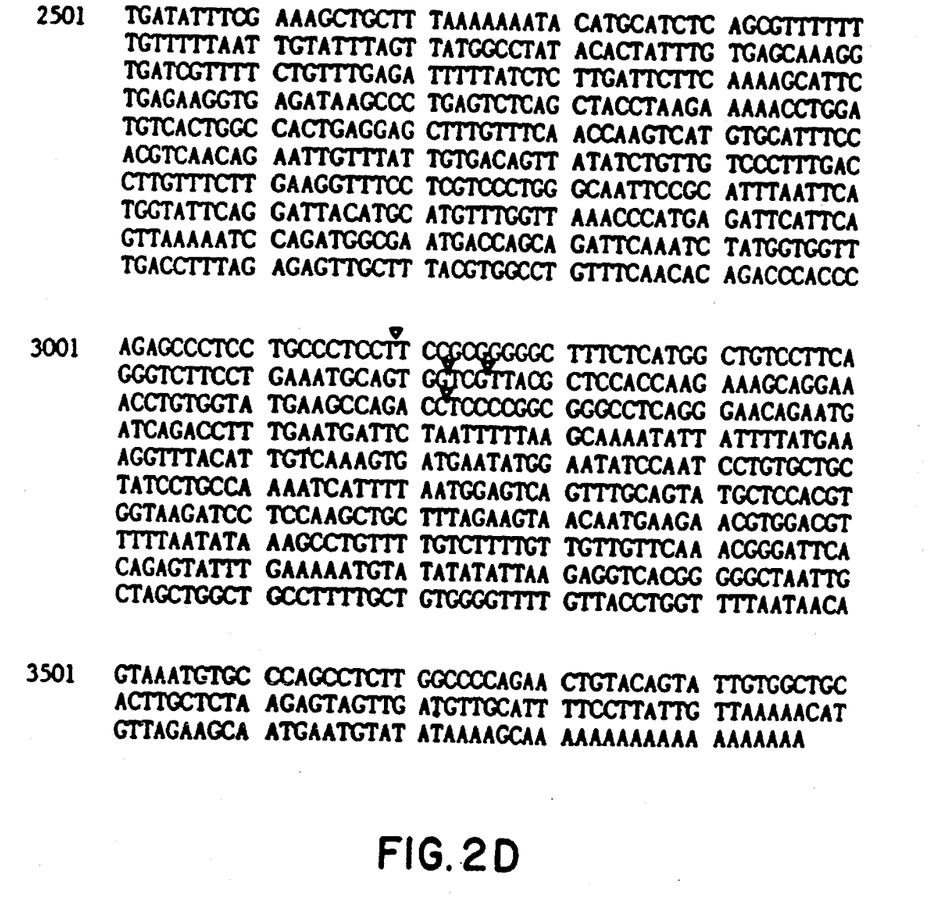

A cDNA library from polyA$^+$ mRNA of the pre-B-cell leukemia cell line 380 was constructed. Cytoplasmic RNA was extracted by the procedure described in ar-Rushdi, et al (1982) *Sematic Cell Genetics,* Vol. 8, pp. 151–161. PolyA$^+$ RNA was selected by oligo(dT) column chromatography as described in Aviv and Leder, (1972) Proceedings of National Academy of Sciences, USA, Vol. 69, pp. 1408–1412. Double stranded cDNA was synthesized from mRNA by reverse transcriptase (Life Science, Inc., Florida) using oligo(dT) as primer as described in Maniatis et al (1982) *Molecular Cloning,* Cold Spring Harbor Laboratory, Cold Spring Harbor, N.Y. After EcoRI linker ligation, the double stranded cDNA was cloned with lambda gt 11 phage vectors, Young and Davis (1983) Proceedings of the National Academy of Sciences, USA, Vol. 80, pp. 1194–1198. By screening approximately $2\times10^5$ recombinant clones with a DNA probe consisting of a segment of chromosome 18 which spans the hotspot of break-points of the translocation of chromosome 18 to chromosome 14, three independent cDNA clones were obtained which are overlapping (B3, B4, and B10). As shown in FIG. 1, clone B3 contains nineteen A residues at the end, indicating that this clone represents the 3' end of the mRNA. The restriction maps of the cDNA clones and genomic sequences are collinear from the 3' end of cDNA clone B3 until just before the BamHI site of the cDNA sequence. The cDNA sequence just beyond this point diverges from the genomic sequence. Thus, the cDNA sequences consist of at least two genomic regions.

When the 5' part of cDNA clone B4 (5' end to the BamHI site) is used to probe the cDNA bank, another set of clones is obtained. including clone B15 and clone B16 (see FIG. 1). These two cDNA clones have the same sequences at the 5' region as does clone B4, but they have totally different sequences at the 3' region than do clones B3, B4, and B10. Thus cDNA cloning has yielded two different sets of clones, indicating that the bcl-2 gene is transcribed into at least two different mRNAs.

In order to obtain cDNA sequences further upstream (in the 5' direction), a cDNA library was constructed using the primer extension method. An oligonucleotide (15-mer) was synthesized and used as a primer for reverse transcriptase as described in Maniatis, supra, and in Gubler and Hoffman (1983) Gene, Vol. 25, pp. 263–269. Three clones were obtained by this method, clone B6-3, B22-1, and B9.

EXAMPLE II

Two different probes were used to visualize the mRNA species corresponding to the bcl-2 gene in Northern blot hybridizations. The first probe (probe A in FIG. 1) contains genomic DNA of chromosome 18 which spans the breakpoint hotspot and also corresponds to the 3' exon. The other probe used was cDNA clone B22-1 which corresponds to the 5' exon (the first exon) RNA was glyoxalated, run on 1% agarose gels, and blotted to nitrocellulose filters as described in Thomas, Proceedings of the National Academy of Sciences, USA (1980) Vol. 77, pp. 5201–5205. The nitrocellulose filter was hybridized with $^{32}$P-labelled probe in 50% formamide, 4 X SSC, 0.1% SDS at 37° C. and finally washed with 2 X SSC (0.3M NaCl, 0.03M Na-citrate, pH 7) at 65° C.

The genomic DNA probe A detected two transcripts, 8.5 kb and 5.5 kb in length. The cDNA probe B22-1 detected the same transcripts as probe A, as well as an additional transcript of 3.5 kb.

The 8.5 kb mRNA was also shown to hybridize to a genomic DNA robe from chromosome 18 which is 3' to genomic probe A (and is indicated in FIG. 1 as probe B).

These data indicate that the bcl-2 gene is transcribed into three mRNAs of different sizes. The possibility that these mRNAs are derived from different but related genes is excluded by the fact that under the same hybridization conditions which were used for the Northern blot hybridization, these probes detect only one cellular gene.

EXAMPLE III

Figure 3:
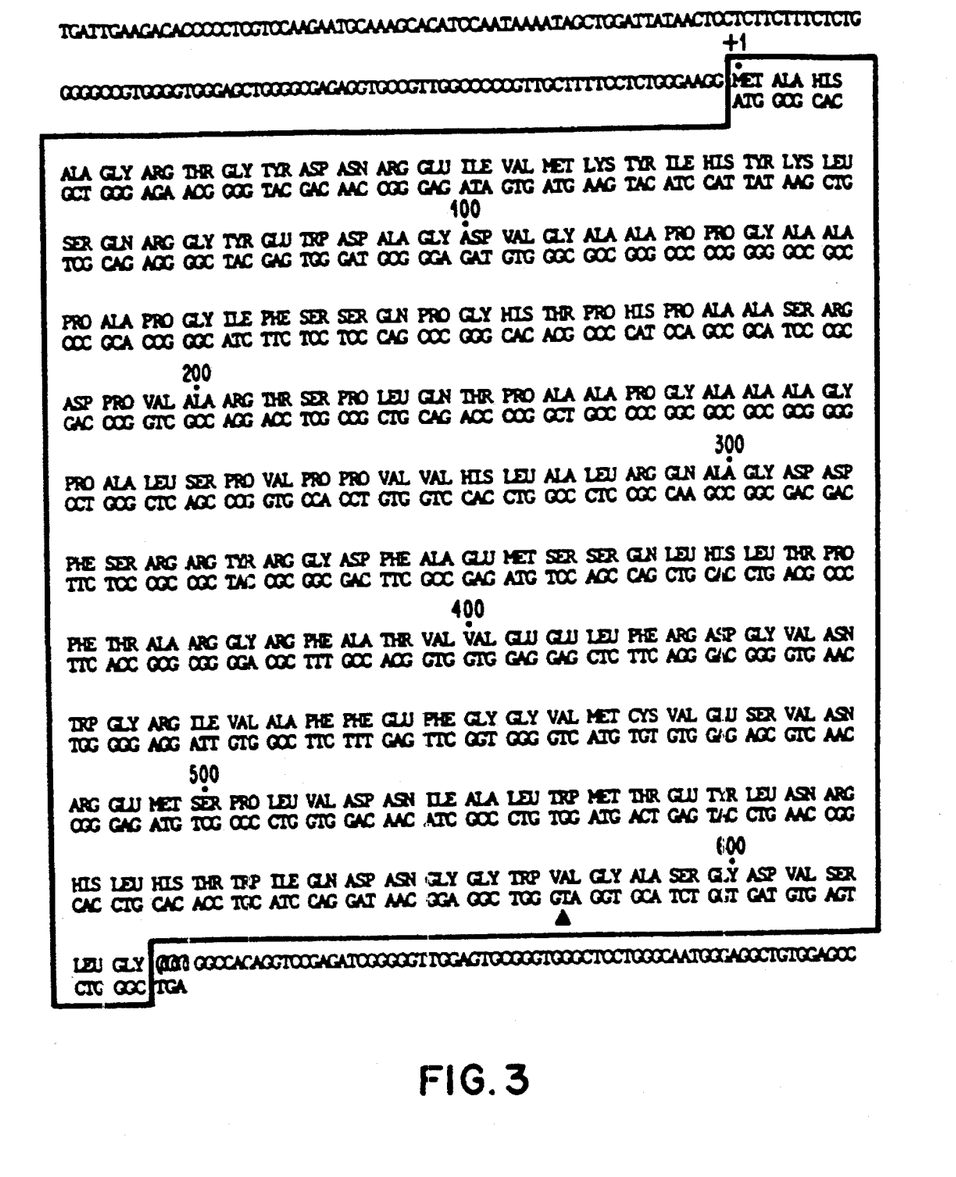
FIG. 3 shows the nucleotide sequence of bcl-2 cDNA corresponding to the 3.5 kb transcript. Only the sequences surrounding the open reading frame are shown.

The nucleotide sequence of overlapping cDNA clones was determined by Maxam and Gilbert's chemical degradation method, (Proceedings of the National Academy of Sciences, USA, Vol. 74, pp. 560–564 (1977), or Sanger's chain termination method, Proceedings of the National Academy of Sciences, USA, Vol. 74, pp. 5463–5467 (1977)). Both strands of DNA were sequenced. The nucleotide sequence derived from the 5.5 kb transcript is shown in FIGS. 2A–2D. The DNA sequence of 5105 base pairs (bp) reveals one possible open reading frame consisting of 239 amino acid residues (bcl-2-alpha). The nucleotide sequence corresponding to the 3.5 kb transcript is shown in FIG. 3. This transcript codes for a protein consisting of 205 amino acid residues (bcl-2-beta), which differs from the bcl-2-alpha protein at the carboxyl terminus.

We claim:

1. A preparation of antibody which is (a) immunoreactive with a human bcl-2 protein selected from the group consisting of bcl-2-$\alpha$ and bcl-2-$\beta$, and which is (b) not immunoreactive with other human proteins.

2. The preparation of claim 1 which is immunoreactive with both bcl-2-$\alpha$ and bcl-2-$\beta$.

3. The preparation of claim 1 which has been purified from an animal antiserum.

4. The preparation of claim 1 wherein the antibody is a monoclonal antibody.

* * * * *